US007645251B2

(12) United States Patent
Hatton et al.

(10) Patent No.: US 7,645,251 B2
(45) Date of Patent: Jan. 12, 2010

(54) ORTHOSIS AND FOOTWEAR ATTACHMENT MECHANISM FOR SAME

(76) Inventors: Dale L. Hatton, 50 Yellow Rose La., Mt. Ida, AR (US) 71957; Zane G. Wallace, 98 Wallace Trl., Story, AR (US) 71970; Gary W. Horton, #5 O'Donnell Ct., Little Rock, AR (US) 72205

( * ) Notice: Subject to any disclaimer, the term of this patent is extended or adjusted under 35 U.S.C. 154(b) by 83 days.

(21) Appl. No.: 11/524,726

(22) Filed: Sep. 21, 2006

(65) Prior Publication Data
US 2007/0073206 A1 Mar. 29, 2007

Related U.S. Application Data

(60) Provisional application No. 60/719,005, filed on Sep. 21, 2005.

(51) Int. Cl.
*A61F 5/00* (2006.01)
*A61F 5/14* (2006.01)
*A43B 7/24* (2006.01)

(52) U.S. Cl. .................. 602/27; 602/1; 602/5; 602/23; 602/28; 602/16; 602/12; 36/140; 36/142; 36/144; 36/155; 36/156; 36/157; 36/158

(58) Field of Classification Search ............. 602/1, 602/5, 23, 27, 28, 29, 16, 12; 36/140, 142, 36/144, 155–158
See application file for complete search history.

(56) References Cited

U.S. PATENT DOCUMENTS

| 3,777,747 | A | * | 12/1973 | Friedman | 602/24 |
|---|---|---|---|---|---|
| 4,088,129 | A | * | 5/1978 | DiGiulio | 602/23 |
| 4,249,523 | A | * | 2/1981 | Bidwell | 602/24 |
| 5,470,310 | A | * | 11/1995 | Sutcliffe | 602/24 |
| 7,267,657 | B1 | * | 9/2007 | Mitchell | 602/29 |
| 2007/0088240 | A1 | * | 4/2007 | Dobbs | 602/5 |

* cited by examiner

*Primary Examiner*—Patricia M Bianco
*Assistant Examiner*—Tarla R Patel
(74) *Attorney, Agent, or Firm*—J. Charles Dougherty

(57) ABSTRACT

A quick-release mechanism for disconnecting the footwear and footplate of an orthoses from a rotation bar, 90-degree bar, or other component of an orthosis is disclosed. The mechanism allows the footwear to be fitted to a patient with the bar or other component disengaged, while also allowing the angle between the bar or other component and the footplate to be locked when the orthosis is in place in order to treat conditions such as clubfoot.

13 Claims, 5 Drawing Sheets

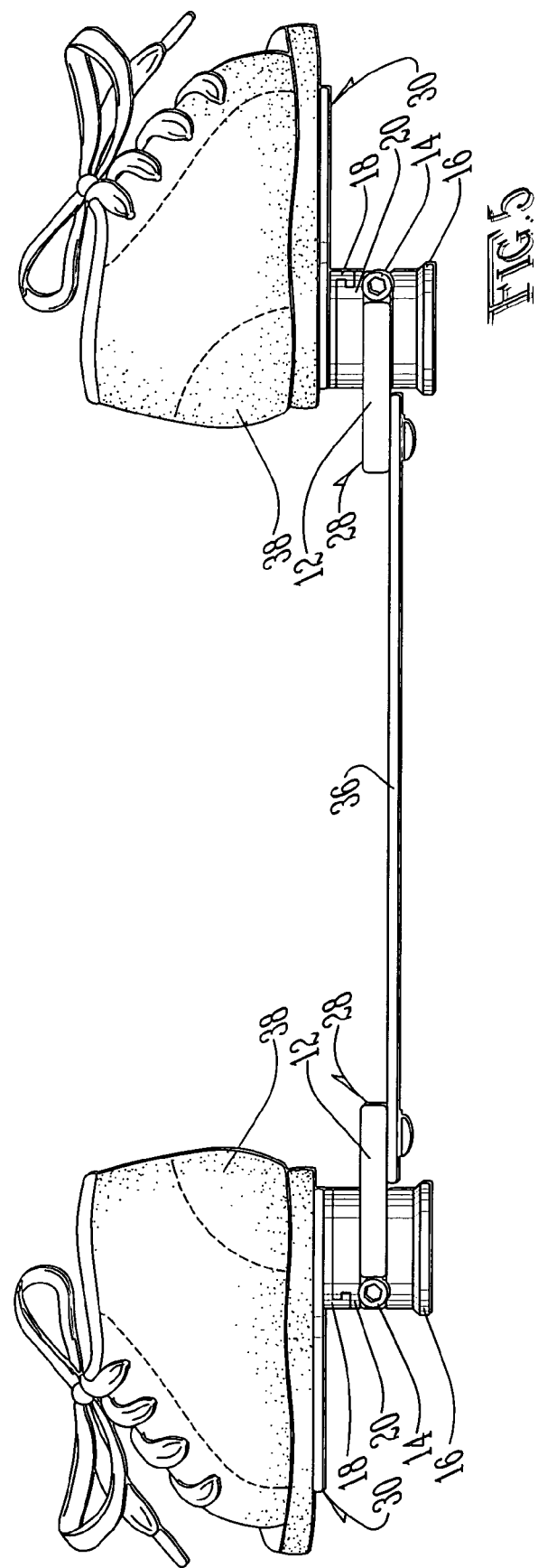

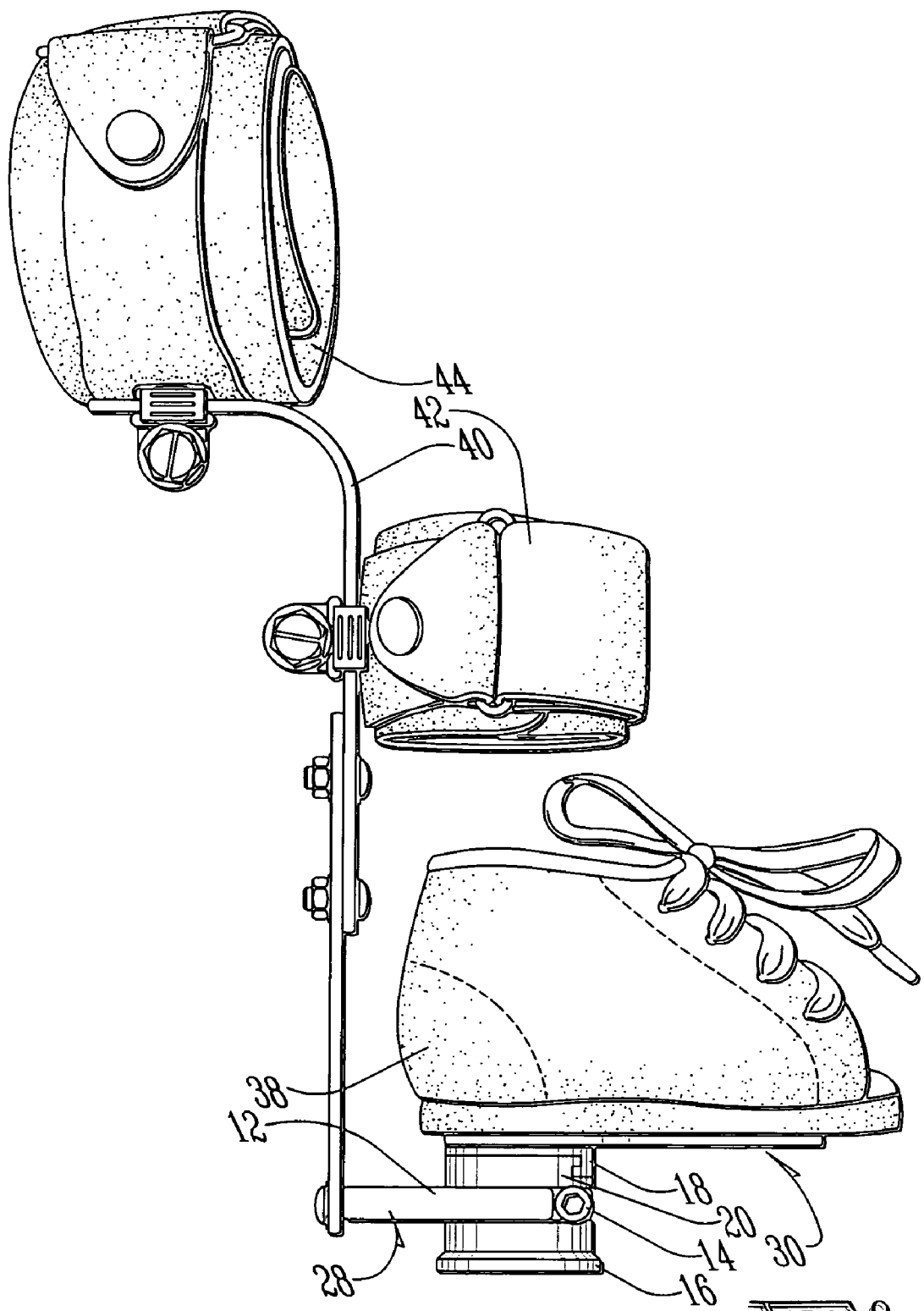

ORTHOSIS AND FOOTWEAR ATTACHMENT MECHANISM FOR SAME

This application claims the benefit of U.S. provisional patent application No. 60/719,005, entitled "Orthosis and Shoe Attachment Mechanism for Same," filed on Sep. 21, 2005. The complete disclosure of such application is hereby incorporated by reference.

BACKGROUND OF THE INVENTION

Clubfoot (talipes equinovarus) is a general term used to describe a range of unusual positions of the foot. Most types of clubfoot are congenital. The most common treatment for congenital clubfoot utilizes non-surgical casting or splinting, or a combination of both, with the treatment regimen beginning shortly after the patient's birth. The purpose of each step in the treatment is to move the affected foot (or feet, in the case of bilateral treatment) into the most normal position possible, and hold that position until the next treatment. These treatments are generally repeated every 1 to 2 weeks for a period of 2 to 4 months, moving the affected foot a little closer to a desired position each time. After treatment is complete, the patient usually wears a brace for an additional period of time in order to keep the clubfoot from beginning to form again. The type of brace chosen may depend upon the position of the patient's foot prior to casting or splinting, and other factors.

A rotation bar is one commonly used element employed in a clubfoot treatment regimen to either internally or externally rotate the patient's foot and leg. A rotation bar is a transverse bar extending between two special shoes, boots, or other footwear worn by the patient. Footplates are screwed, riveted, or otherwise attached to the soles of each of the shoes, and the bar is connected to the footplates at each end. An adjustable screw is used to hold the bar to each of the footplates. These screws may be loosened manually to adjust the angle of the shoe with respect to the bar. The degree of rotation internally or externally for each foot is thus set by rotating the corresponding footplate with respect to the bar, and then locking the footplate into a statically held position by tightening the screw connecting the bar and footplate. It should be noted that the bar may be a solid bar with various available lengths depending upon the size of the patient, or it may be a lap-over bar that is slotted to allow for adjustment of the separation between the patient's feet.

From the above description of the typical rotation bar it will be understood that, because the patient's shoes are fastened to the footplates by screws, rivets, or the like, the shoes are not intended to be removed from the bar during normal use of the device. Instead, the shoes are generally left attached to the rotation bar while being fitted onto and removed from the patient's feet.

Another common type of brace used in clubfoot treatment is a "90-degree brace." Like the rotation bar, the 90-degree brace includes a footplate that is screwed or riveted to a shoe, boot, or other footwear, which is then fitted to the patient's foot. The purpose of the 90-degree brace, however, is to hold the patient's foot in a certain position with respect to the corresponding leg rather than the opposing foot. The brace fits under the foot at the footplate, has a 90-degree bend to travel up the back of the calf, and another 90-degree bend to follow under the knee and up the back of the thigh. The brace typically includes a calf and thigh band for attachment. The purpose of a 90-degree brace is to keep the knee and foot bent precisely at 90 degrees, and may be used unilaterally or bilaterally. By having the knee held at a 90-degree bend, the brace prevents the knee from going into extension, and therefore holds the foot and the shoe more effectively in the desired position with respect to the leg orientation. As with the rotation bar, the 90-degree brace generally attaches to the footplate with a screw that may be adjusted to control the angle of rotation between the footplate and brace.

Since the patient using orthotic devices such as the rotation bar and 90-degree brace described above is typically an infant, the brace must be routinely fitted and removed by a parent, guardian, or other adult. This process is complicated by the fact that infants will often resist any efforts to place shoes upon their feet. Because the brace is attached to the shoes at the footplates in such a manner that it may not be easily removed, the shoe is generally fitted with the brace still attached, rendering the process of fitting the shoe or shoes to the infant quite difficult. The person performing the fitting must position the shoe properly with respect to the patient's foot, while simultaneously ensuring that the attached brace does not swing about and injure the infant or the person performing the placement. In the case of a rotation bar, the person performing the fitting must then fit the other foot in the remaining shoe while both safely restraining the infant and positioning the foot and shoe for fitting. In the case of a 90-degree brace, the person performing the fitting must adjust the calf and thigh bands for a comfortable but secure fitting while preventing injury to the infant due to movement of the brace caused by the infant's foot movements. It would be desirable to fit the associated shoe or other footwear to the patient without the brace attached in order to simplify this procedure and reduce the chance of injury to the patient. What is desired then is a method of securely attaching the footwear to the orthosis that would allow the footwear to be easily removed and reattached for fitting of the footwear and orthosis to the patient.

SUMMARY OF THE INVENTION

The present invention is directed both to a quick-release footwear attachment mechanism for orthoses and to a complete orthosis that comprises the quick-release attachment mechanism. While two particular types of orthoses are described herein with respect to this snap-lock attachment mechanism, the invention is not so limited, and may be employed with other types of orthoses wherever footwear is attached to a brace or bar mechanism. Furthermore, while the use of orthoses for the treatment of clubfoot is provided herein as an example, the invention is not limited to treatment of this condition, but may be used with respect to orthoses employed for the treatment of various other conditions as well.

It is therefore an object of the present invention to provide for a mechanism that allows for the disengagement between footwear and a bar or brace of an orthosis to simplify the fitting of the footwear.

It is a further object of the present invention to provide for an easier and safer means of fitting footwear associated with an orthosis to a patient, particularly where the patient is an infant.

It is also an object of the present invention to provide for a quick-release mechanism for the attachment of footwear to an orthosis that allows the angle of the footwear to the orthosis to be adjusted.

These and other features, objects and advantages of the present invention will become better understood from a consideration of the following detailed description of the preferred embodiments and appended claims in conjunction with the drawings as described following:

DETAILED DRAWINGS OF THE PREFERRED EMBODIMENTS

FIG. 5 is a perspective view of a rotation bar orthosis according to a preferred embodiment of the present invention.

FIG. 6 is a perspective view of a 90-degree brace orthosis according to a preferred embodiment of the present invention.

DETAILED DESCRIPTION OF THE PREFERRED EMBODIMENTS

Figure 1:
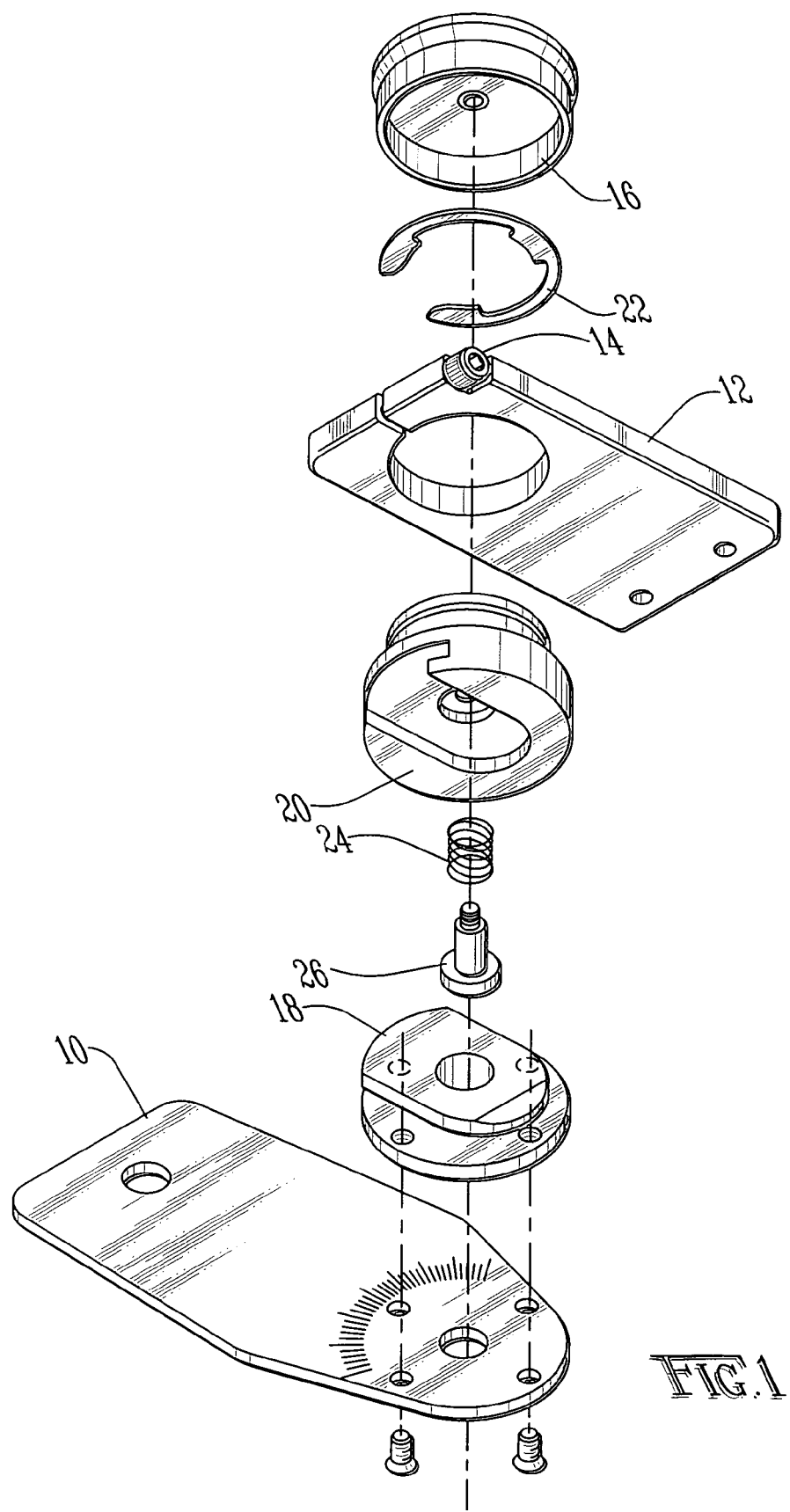
FIG. 1 is an exploded view of the components of a quick-release mechanism according to a preferred embodiment of the present invention.
Figure 2:
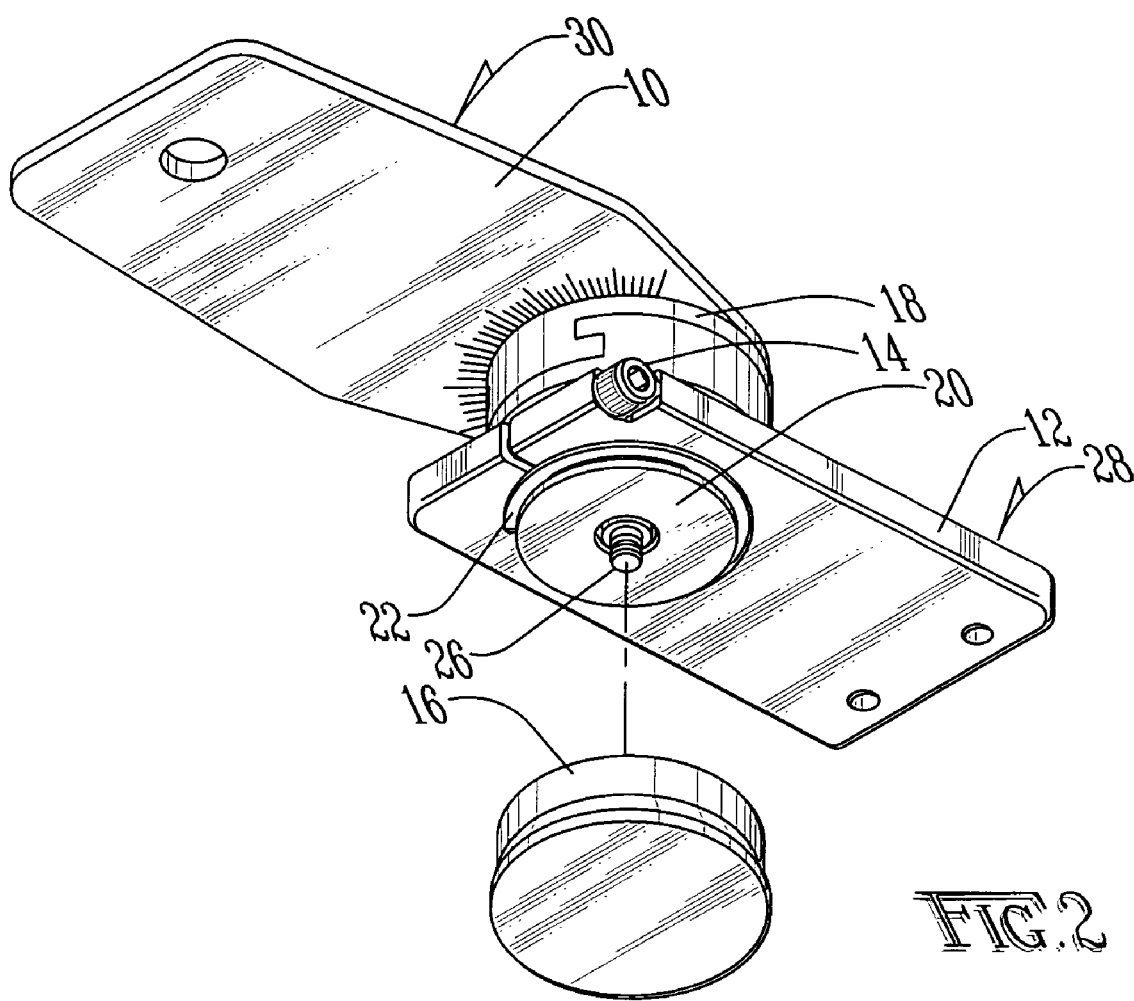
FIG. 2 is a detail view of the retaining clip and button portion of a quick-release mechanism with the cover plate removed according to a preferred embodiment of the present invention.

With reference to FIGS. 1-4, a preferred embodiment of a quick-release mechanism for an orthosis according to the present invention may be described. As shown particularly in FIG. 3, the quick-release mechanism comprises two separate assemblies, brace assembly 28 and footplate assembly 30. These two assemblies may be snapped together to form a secure lock, and may be easily and quickly released from each other, as will be described below.

Footplate assembly 30 is comprised of footplate 10 and footplate fitting 18. Footplate fitting 18 is preferably attached to footplate 10 by screws, rivets, or the like. These screws, rivets, or like fasteners may also be used to attach footwear 38 (as shown in FIGS. 5 and 6) to footplate 10. Alternatively, footplate 10 and footplate fitting 18 may be formed of a single, integral part, or footplate 10 may be omitted and footplate fitting 18 attached directly to footwear 38.

Figure 3:
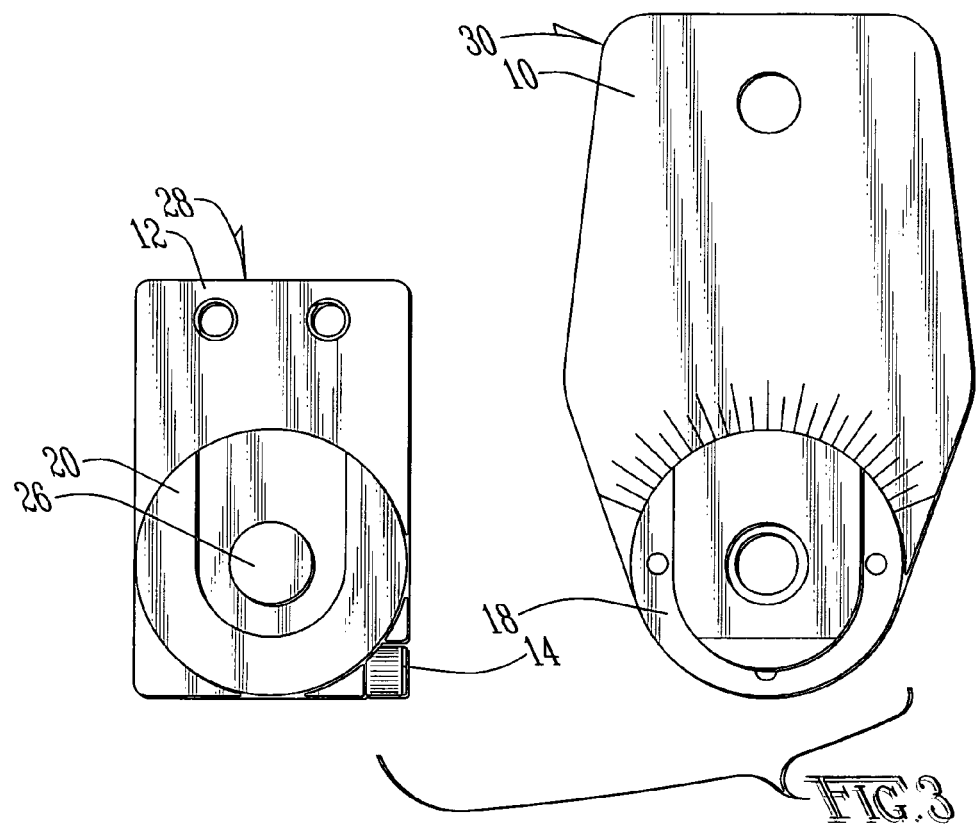
FIG. 3 is a top plan view of the two interlocking assemblies of a quick-release mechanism according to a preferred embodiment of the present invention, showing the mechanism disengaged.

Brace assembly 28 is composed of brace attachment plate 12, brace attachment plate set screw 14, brace fitting 20, release button 26, release spring 24, knob 16, and lock ring 22. These various parts are shown disassembled (along with the parts for footplate assembly 30) in FIG. 1. Brace attachment plate 12 is preferably formed of a relatively thick plate, with a circular opening sized to receive a lower cylindrical portion of brace fitting 20. A slot extends between such hole and the edge of brace attachment plate 12, providing a gap that is crossed by a transverse tapped hole sized to receive set screw 14. When brace fitting 20 is inserted into the circular opening of brace attachment plate 12 as depicted in FIG. 3, set screw 14 may be tightened to lock brace fitting 20 in place and prevent further rotational movement of brace fitting 20 with respect to brace attachment plate 12. As will explained below, this mechanism serves to lock the angle of footwear 38 with respect to the brace employed with the quick-lock mechanism. Lock ring 22 fits around the lower cylindrical portion of brace fitting 20, which extends through the circular opening in brace attachment plate 12. Lock ring 22 secures brace fitting 20 firmly in place against the face of brace attachment plate 12, but allows rotational movement of brace fitting 20 so long as set screw 14 is sufficiently loosened.

Spring 24 is fitted around the shaft of release button 26 before inserting the shaft of release button 26 through the small opening in the surface of brace fitting 20. Release button 26 is secured in place by screwing the threaded end of the shaft of release button 26 into the tapped hole in the interior of knob 16. Knob 16 is thereby fitted at the opposite side of brace attachment plate 12 from brace fitting 20, being held tight against brace attachment plate 12 by the force of spring 24 biasing the head portion of release button 26 away from brace attachment plate 12. It may be seen then that pulling knob 16 downward and away from brace attachment plate 12 will cause the head of release button 26 to sink into the matching recessed area on the face of the tongue-shaped, grooved portion of brace fitting 20. Releasing knob 16 will cause spring 24 to bias the head of release button 26 back in an upwardly direction, thereby extending the head of release button 26 out of the recessed area on the face of the tongue-shaped grooved portion of brace fitting 20.

Each of the components described above and illustrated in FIG. 1 may be constructed of various materials, provided that such materials provide sufficient strength to withstand the forces inherent upon such components in the use of the preferred embodiment of the present invention. Spring 24 and lock ring 22 are preferably formed of steel for both strength and resiliency. Set screw 14 is preferably formed of steel as well. Brace attachment plate 12, knob 16, release button 26, brace fitting 20, footplate fitting 18, and footplate 10 may preferably be constructed of aluminum or another lightweight metal for the purpose of reducing the weight of the preferred embodiment, and thereby decreasing the discomfort associated with wearing the device for the patient. Numerous other similar strong, lightweight materials may be substituted in alternative embodiments. Footwear 38 may be constructed of any materials normally employed in such applications, including leather and various synthetic fabrics for the upper portion and rubber or leather for the lower portion.

It may be noted that while the preferred embodiment is described with certain components associated with a brace fitting 20 and others with a footplate fitting 18, the relationship of these components to a brace and footplate could be reversed in alternative embodiments. For example, brace fitting 20 could be connected to footplate 10 as part of footplate assembly 30, and footplate fitting 18 could be connected to brace attachment plate 12 as part of brace assembly 28. As additional examples, the relative arrangement of release button 26 and set screw 14 and the related structure could similarly be reversed in alternative embodiments.

Figure 4:
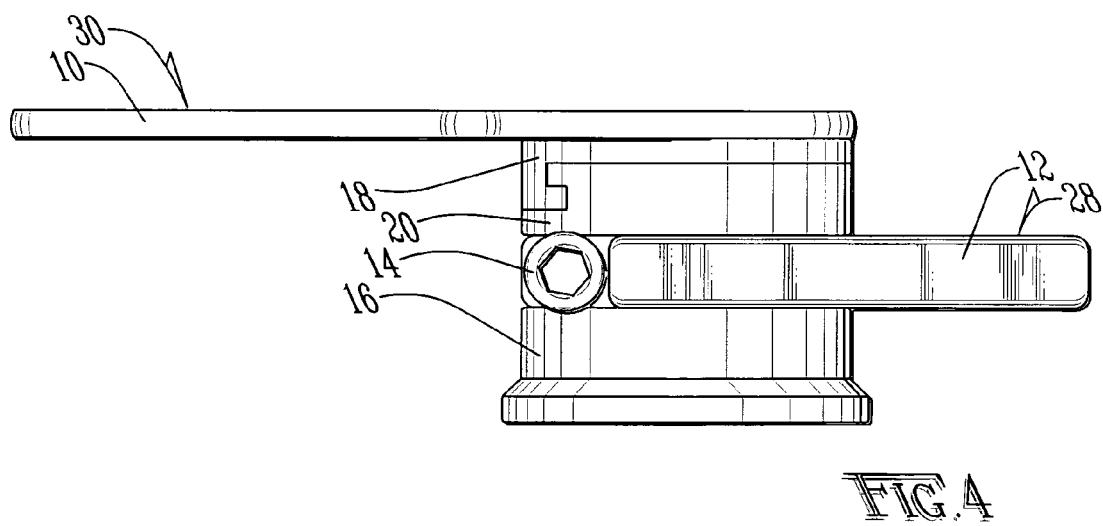
FIG. 4 is a side elevational view of a quick-release mechanism according to a preferred embodiment of the present invention, showing the mechanism engaged.

Referring now particularly to FIGS. 3 and 4, the operation of the quick-release mechanism according to a preferred embodiment of the present invention may be described. It will be seen that the tongue-shaped groove portion of brace fitting 20 is sized to receive the tongue-shaped tab portion of footplate fitting 18. Lateral wings on the tongue-shaped tab portion of footplate fitting 18 may be transversely slid into place within the tongue-shaped groove portion of brace fitting 20. As the insertion operation proceeds, the leading edge of the tab portion of footplate fitting 18 will strike the head portion of release button 26. In the preferred embodiment, this leading edge is beveled in order to smoothly depress release button 26 as the tongue-shaped tab portion of footplate fitting 18 slides over release button 26 and fully into place within brace fitting 20. Once this fully engaged position is reached, the circular opening in footplate fitting 18 that is sized to receive release button 26 will be directly above release button 26, thereby allowing the biasing force of spring 24 to push the head portion of release button 26 upwardly into the circular opening in footplate fitting 18. As a result of this operation, footplate fitting 30 and brace fitting 28 will become securely locked together. The only operation necessary in order to complete the locking of these two assemblies together is to simply slide the matching portions fully together.

In order to release footplate assembly 30 from brace assembly 28, the operator first pulls downwardly on knob 16 of brace assembly 28. Because release button 26 is threaded into knob 16, this downward force causes the depression of the head portion of release button 26 within the matching recess on brace fitting 20. The operator must pull with sufficient force on knob 16 to overcome the biasing force of spring 24. With release button 26 now disengaged from footplate assembly 30, footplate assembly 30 may be slid free from brace assembly 28 in a manner opposite to that described above for locking these two assemblies together.

Referring now to FIGS. 5 and 6, two orthoses may be described incorporating the quick-release mechanism according to a preferred embodiment of the present invention. In FIG. 5, a brace assembly 28 is attached at either end of a rotation bar 36. In alternative embodiments, brace assembly 28 may be integrated into the brace itself, in this example forming opposite ends of rotation bar 36. Footwear 38 is attached to each of the two matching footplate assemblies 30. Although the illustrated embodiment shows a solid rotation bar 36, a two-piece bar with a sliding bolt to hold them together may be used to provide a rotation bar 36 of adjustable length in alternative embodiments. In FIG. 6, a single brace assembly 38 is connected to a 90-degree brace 40, which further comprises a calf strap 42 and thigh strap 44 to hold the 90-degree brace 40 in place with respect to the patient's leg. A footplate assembly 30 is fitted to the brace assembly 38 in the manner described above, and footwear 38 is attached for fitting to the patient. It may be noted that in the preferred embodiment of FIG. 6, 90-degree brace 40 is of a two-piece adjustable type that is bolted together, but alternative embodiments may employ a single-piece type of 90-degree brace 40.

In either the case of brace assembly 28 or brace assembly 38, as depicted in FIGS. 5 and 6, respectively, an alternative embodiment of the invention comprises the positioning of footplate or footplates 10 at an angle. In a particular alternative embodiment, footplate or footplates 10 are positioned such that the forward end of footplate or footplates 10 (toward the patient's toes) rises at about 10 degrees above the horizontal plane. Some doctors recommend this positioning because it is believed that the angling of the patient's toes upward serves to stretch the tendons at the heel, thereby enhancing the treatment. This positioning may be accomplished by bending the brace assembly 28 or 38 itself, or more preferably is accomplished by mounting brace fitting 20 at an angle such that when footplate assembly 30 is engaged it causes footplate 10 to be inclined at the appropriate angle.

In fitting either the braces of FIG. 5 or 6 to the patient, a similar procedure is employed. First, footwear 38 is removed from the applicable brace by pulling downwardly on the appropriate knob 16, thereby releasing the locking mechanism, and pulling transversely such that the appropriate footplate assembly 30 slides away from the corresponding brace assembly 28. Footwear 38 may then be conveniently fitted to the patient in the manner of any other footwear. Once footwear 38 is fitted to the patient, then the appropriate footplate assembly 30 may be slid back into engagement with the corresponding brace assembly 28, thereby locking the device into position for use in connection with the patient's treatment. It may be noted that the design of the release mechanism in the preferred embodiment encompassing rotation bar 36 is such that right and left footplate assemblies 30 are clearly distinguishable, and thus the left and right shoes cannot easily be inadvertently reversed and placed on the wrong ends of rotation bar 36.

As already noted, a typical treatment regimen involves the periodic adjustment of the angle of the patient's foot with respect to the opposing foot (in the case of rotation bar 36) or with respect to the patient's leg (in the case of 90-degree bar 40). This is accomplished by first loosening set screw 14 of brace attachment plate 12, and then rotating brace fitting 20 such that the tongue-shaped groove of brace fitting 20 forms the appropriate angle with the attached brace. As a convenience to the practitioner, angle markings are preferably provided on footplate 30 to serve as a guide in this adjustment process, as shown in FIG. 3. While typically this adjustment would be made when brace assembly 28 is connected to footplate assembly 30, such that these angle markings may be employed, the adjustment could also be made when the two assemblies are not connected. Once the appropriate adjustment is made, set screw 14 is again tightened to lock the brace into place with the appropriate angle. Use of the footwear 38 attachment mechanism does not require adjustment of set screw 14, and thus the parent or guardian responsible for fitting and removing the brace on a regular basis need not be concerned with the adjustment of the angle setting of the device, which would typically be performed only by an appropriate professional.

The present invention has been described with reference to certain preferred and alternative embodiments that are intended to be exemplary only and not limiting to the full scope of the present invention as set forth in the appended claims.

We claim:

1. An orthotic apparatus, comprising:
    (a) a brace;
    (b) a brace fitting, wherein said brace fitting is rotatably connected to said brace, and wherein said brace fitting comprises an adjusting member operable to selectively lock and unlock rotation of said brace fitting with respect to said brace;
    (c) a footplate fitting, wherein said footplate fitting is removably connectable to said brace fitting; and
    (d) a tongue-shaped tab portion connected to one of said brace fitting and said footplate fitting, wherein said tab portion is slideably engageable with a tongue-shaped groove portion sized to receive said tab portion on that one of said brace fitting and said footplate fitting not connected to said locking member.

2. The orthotic apparatus of claim 1, further comprising a spring operable to bias said locking member toward a disengaged position with that one of said brace fitting and said footplate fitting not connected to said locking member.

3. The orthosis of claim 2, wherein said spring comprises a release button attached to extend transversely into said tongue-shaped groove portion, and wherein said tab portion further comprises a circular opening sized to receive said button when said tab portion is fitted within said tongue-shaped groove portion.

4. The orthotic apparatus of claim 1, further comprising one of a footplate and a footwear connected to said footplate fitting.

5. The orthotic apparatus of claim 1, wherein said brace comprises a 90-degree brace.

6. The orthotic apparatus of claim 1, wherein said brace comprises a rotation bar.

7. The orthotic apparatus of claim 6, wherein said rotation bar comprises first and second ends, one of said brace fitting and said footplate fitting is connected to said rotation bar at about said first end, and further comprising a second brace fitting and second footplate fitting, wherein one of said second brace fitting and said second footplate fitting is connected to said rotation bar at about said second end.

8. An orthosis, comprising:
(a) a footplate;
(b) a footplate fitting attached to said footplate, wherein said footplate fitting comprises a tongue-shaped tab portion;
(c) a brace;
(d) a brace attachment plate attached to said brace; and
(e) a brace fitting attached to said brace attachment plate, wherein said brace fitting comprises a tongue-shaped groove portion sized to slideably engage said tab portion whereby said footplate and said brace may be releasably joined together.

9. The orthosis of claim 8, wherein said brace fitting further comprises a button extending perpendicularly through said tongue-shaped groove portion, and said footplate fitting further comprises a circular opening in said tab portion sized to receive said button.

10. The orthosis of claim 9, further comprising a spring in communication with said button wherein said button is biased into said slot portion and towards said circular opening in said tab portion when said tab portion is engaged with said tongue-shaped groove portion.

11. The orthosis of claim 8, further comprising a set screw engageable with said brace attachment plate and operable to hold said brace fitting to said brace attachment plate.

12. The orthosis of claim 8, wherein said brace fitting extends through an opening in said brace attachment plate, said brace fitting comprises an upper end and a lower end, wherein said upper end extends above said brace attachment plate and said lower end extends below said brace attachment plate, said tongue-shaped groove portion appears at said upper end of said brace fitting, and a lock ring attaches at said lower end of said brace fitting whereby said brace fitting is prevented from slipping away from said brace attachment plate.

13. The orthosis of claim 12, further comprising a release knob, wherein said release knob attaches to said button at said lower end of said brace fitting whereby pulling said release knob downward disengages said button from said circular opening in said tab portion of said footplate fitting.

* * * * *